United States Patent [19]

Post et al.

[11] Patent Number: 5,402,148

[45] Date of Patent: Mar. 28, 1995

[54] MULTI-RESOLUTION VIDEO APPARATUS AND METHOD FOR DISPLAYING BIOLOGICAL DATA

[75] Inventors: William L. Post; Paolo Fontani, both of McMinnville, Oreg.

[73] Assignee: Hewlett-Packard Corporation, Palo Alto, Calif.

[21] Appl. No.: 962,368

[22] Filed: Oct. 15, 1992

[51] Int. Cl.6 .............................................. G09G 1/06
[52] U.S. Cl. ...................................... 345/132; 345/213
[58] Field of Search ................ 340/799, 747, 721; 315/383; 345/132, 133, 213, 115, 24, 116; 307/267

[56] References Cited

U.S. PATENT DOCUMENTS

| | | | |
|---|---|---|---|
| 3,793,626 | 2/1974 | Zambuto | 345/24 |
| 4,435,779 | 3/1984 | Mayer et al. | 345/133 |
| 4,684,936 | 8/1987 | Brown et al. | 345/116 |
| 4,847,641 | 7/1989 | Tung. | |
| 4,924,522 | 5/1990 | Bray et al. | 345/132 |
| 5,005,139 | 4/1991 | Tung | 364/519 |
| 5,027,212 | 6/1991 | Marlton et al. | 345/213 |

Primary Examiner—Alvin E. Oberley
Assistant Examiner—Vivian Chang

[57] ABSTRACT

A method for simultaneously displaying images of different resolutions on a single raster scan video monitor begins with the step of storing lower resolution text and graphics data in a first memory. The data in the first memory is used to generate a first video frame having N1 pixels per line. A first video data stream is generated from the first memory at a first rate corresponding generally to the bandwidth of the video monitor. Higher resolution biological waveform data is stored in a second memory. The data in the second memory represents a second video frame having N2 pixels per line. If desired, the second memory can include data for stationary and scrolling high resolution images. A second video data stream is generated from the second memory at a second rate, which is faster than the first rate. The ratio of the second rate divided by the first rate is approximately equal to N2 divided by N1. The first and second video data streams are combined to produce a single combined video data stream that is displayed on the video monitor.

22 Claims, 16 Drawing Sheets

MULTI-RESOLUTION VIDEO APPARATUS AND METHOD FOR DISPLAYING BIOLOGICAL DATA

BACKGROUND OF THE INVENTION

This invention relates generally to a video graphics system and, more particularly, to a low cost method and apparatus for combining relatively low resolution text and graphics normally displayed on a home computer video monitor with relatively high resolution graphics normally displayed on a relatively high resolution vector monitor.

Raster scan display devices are typically used to display relatively low resolution text and graphics images. As is well known in the art, the electron beam from a cathode ray tube scans across the entire monitor screen, one line at a time, in response to horizontal and vertical sync signals. The scan pattern is repeated about 60–72 times per second and the resultant image is integrated by the human eye. A typical raster scan image can exhibit aliasing, which depends upon the size of the displayed pixels and is characterized by jagged edges on a sharply sloped line segment, instead of a smooth edge.

Vector displays are typically used to display relatively high resolution images such as are found in a cardiographic ECG waveform, or other biological waveforms. As is well known in the art, the position of the electron beam from the cathode ray tube is controlled by orthogonal plates and can be moved from one point on the display screen to any other point. A repetitive waveform can be constantly written to the screen, under control of an input sync waveform, which can be the input signal itself, or other waveforms such as the power line waveform. Vector waveforms do not exhibit aliasing, because even sharply sloped line segments are constructed of a single sweep of the electron beam, and not successive scanned lines.

Lower resolution text and graphics provided by a home computer are easily combinable with the relatively higher resolution biological waveforms if an expensive high resolution (one million pixels or more) raster scan display is used, although some aliasing can still be present. The two different resolution graphics images are typically not combinable on a single vector display.

Accordingly, a need remains for a convenient method and apparatus for combining lower resolution text and graphics with higher resolution biological waveforms without the use of an expensive high resolution raster scan video monitor.

SUMMARY OF THE INVENTION

According to the present invention, a method for simultaneously displaying images of different resolutions on a single raster scan video monitor begins with the step of storing lower resolution text and graphics data in a first memory. The data in the first memory is used to generate a first video frame having N1 pixels per line. A first video data stream is generated from the first memory at a first rate corresponding generally to the bandwidth of the video monitor. Higher resolution biological waveform data is stored in a second memory. The data in the second memory represents a second video frame having N2 pixels per line. The ratio of the number of pixels per line, i.e., N2 divided by N1, is approximately equal to the resolution of the second video stream divided resolution of the first video stream. If desired, the second memory can include data for stationary and scrolling high resolution images. A second video data stream is generated from the second memory at a second rate, which is faster than the first rate. The ratio of the second rate divided by the first rate is approximately equal to N2 divided by N1. The first and second video data streams are combined to produce a single combined video data stream that is displayed on the video monitor.

It is, therefore, a principal object of the invention to combine images of different resolutions on a single raster scan monitor.

It is another object of the invention to display a combined video image with enough resolution to significantly reduce aliasing in the higher resolution image.

Another object of the invention is to provide a first higher resolution video plane for displaying static information and a second higher resolution video plane to display scrolling data.

A further object of the invention is to allow the apparatus associated with the higher resolution video to operate in conjunction with a standard VGA card, as well as Super VGA and Ultra VGA cards.

The foregoing and other objects, features and advantages of the invention will become more readily apparent from the following detailed description of a preferred embodiment of the invention which proceeds with reference to the accompanying drawings.

DETAILED DESCRIPTION

Figure 1:
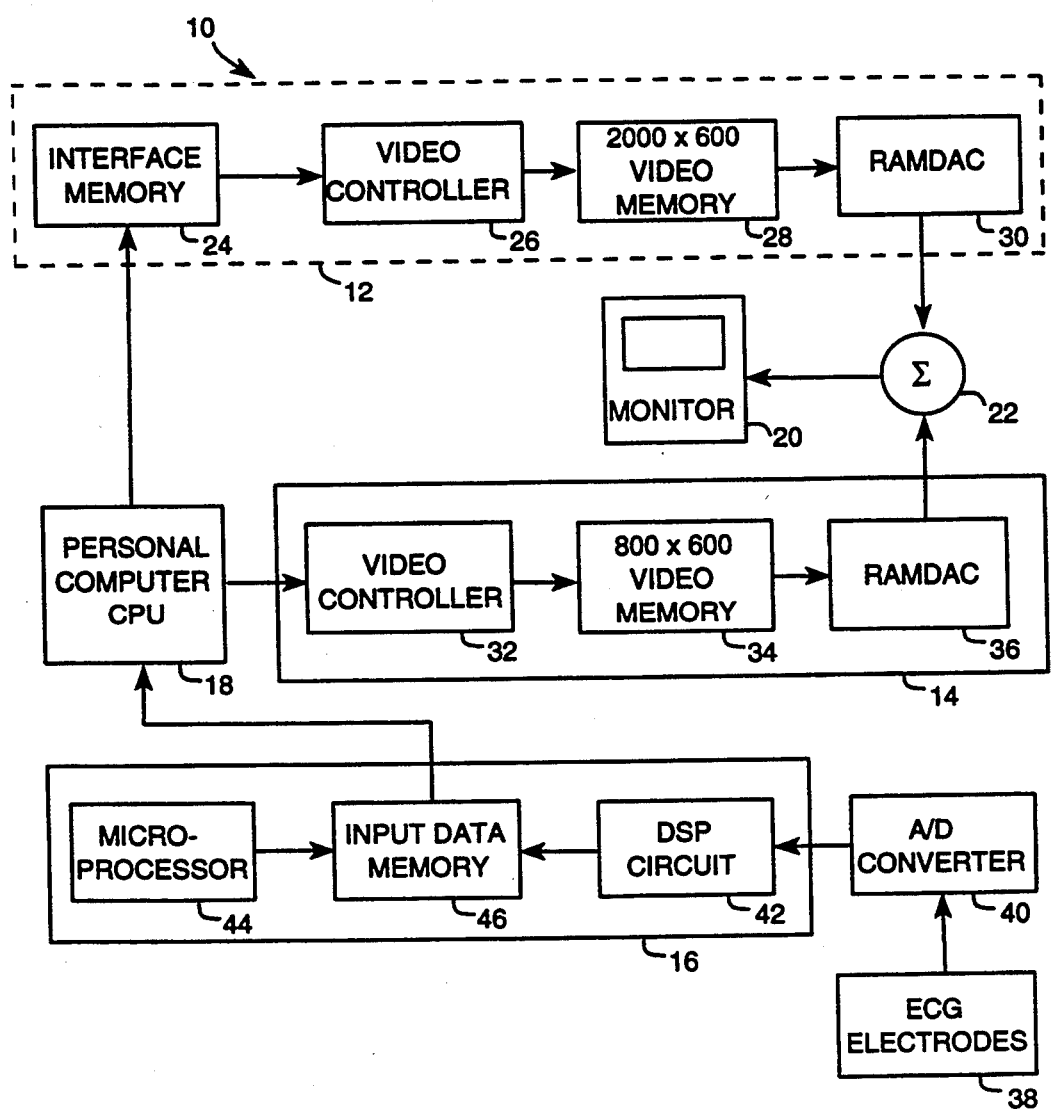
FIG. 1 is a block diagram of the entire video graphics system of the present invention.

Referring now to FIG. 1 the block diagram of the entire video graphics system 10 of the present invention includes a high speed video graphics card 12, a low speed graphics card 14, a data acquisition card 16, a personal computer CPU 18 and monitor 20. The cards can be separate, etched circuit boards housed in the personal computer. Graphics cards 12 and 14 can be combined on a single graphics card, if desired. The data acquisition card 16 receives analog data such as biological data from a patient monitored by ECG electrodes 38. The analog data is digitized in A/D converter 40 and delivered to the data acquisition card 16. The digital data can be filtered or otherwise acted upon in the digital signal processing ("DSP") circuit 42. Once processed, the digital data is delivered to an input data memory 46 under control of a microprocessor 44. The personal computer receives the processed data from the data acquisition card 16, stores the data to its hard disk after performing any necessary formatting, and delivers the data directly to the low speed video card 14, and indirectly to the video controller 26 through interface memory 24.

Both the low and high speed video cards 12 and 14 include a video controller, a video memory, and a RAMDAC. The video controller 32 in the low speed video card 14 directly receives data from the CPU 18, along with accompanying display commands, which is stored on the 800×600 video memory 34. Other video memory configurations are possible, e.g., 1024×768, or any other desired configuration, depending on the amount of video memory available on the low speed video card 14. The RAMDAC 36 converts the data stream from memory 34 into analog RGB currents, which are directed to one of the inputs of the summer circuit 22.

Similarly, the video controller 26 in the highspeed video card 12, which can be, for example, an 80960CA integrated circuit manufactured by Intel Corporation of Santa Clara, Calif., indirectly receives data from the CPU 18 through interface memory 24. The video controller 26 performs any additional filtering necessary on the incoming data from the CPU 18, converts the data into pixel data, and stores the pixel data into video memory 28. The video controller 26 also determines what data is displayed on the screen, and controls the scrolling and coloring of the image. The configuration of the video memory 28 is determined by the desired resolution and will vary depending on the resolution selected, e.g., 2000×600, 1700×768, or any other configuration. The RAMDAC 30 converts the data stream from memory 28 into analog RGB currents, which are directed to the other of the inputs of the summer circuit 22. The summer circuit 22 combines the analog RGB currents into a combined analog video output and is displayed on the raster scan monitor 20.

Figure 2:
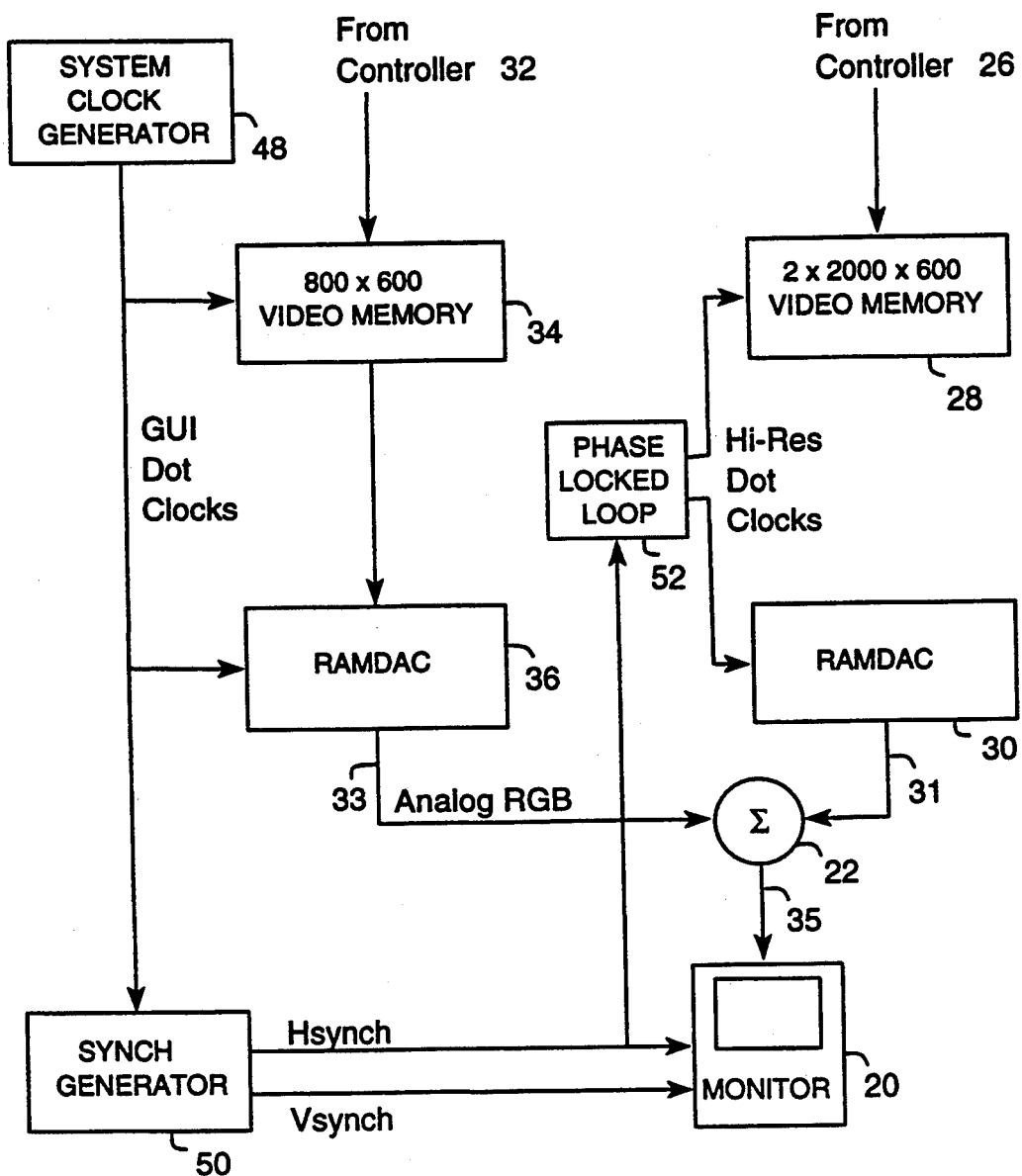
FIG. 2 is a more detailed block diagram of a portion of the video graphics system of FIG. 1.

A more detailed block diagram of the video cards 12 and 14, the summer 22, and monitor 20 is shown in FIG. 2. The video memories 28 and 34 are shown as in FIG. 1, receiving data and control signals from the respective controllers 26 and 32. The outputs of the video memories are each coupled to the inputs of RAMDACs 30 and 36, respectively, through a corresponding multi-pixel data bus, e.g., four pixel data bus. Each pixel is represented by one or more data bits which encode the color information. The number of bits used is determined by the number of possible colors, which is determined by the size of the color palette in the RAMDAC. The outputs of the RAMDACs 30 and 36 are combined in the summer circuit 22 and displayed on the raster scan monitor 20.

In order to provide both horizontal and vertical synchronization between the low resolution and the high resolution video streams, a system clock generator 48 is required. The system clock generator 48 provides a GUI standard dot clock and provides a stimulus from which the vertical synchronization pulse Vsync and the horizontal synchronization pulse Hsync are derived. The video memory 34 dot clock is derived from the RAMDAC 36 dot clock, which is an integer multiple thereof, e.g., multiple of four. A sync generator 50 receives the GUI dot clock to create a 48 KHz horizontal Hsync signal and a 72 Hz vertical Vsync signal for scanning the video data across the video monitor screen. The Hsync signal is also used as an input signal to a phase locked loop circuit 52. The phase locked loop circuit uses a frequency-to-voltage converter and voltage-controlled oscillator, as is known in the art. The phase locked loop generates two high speed clocks, both synchronized to the Hsync pulse. A first clock is provided for RAMDAC 30, and a second clock (first clock divided by an integer multiple, e.g., four) is provided to the video memory 28.

Figure 3:
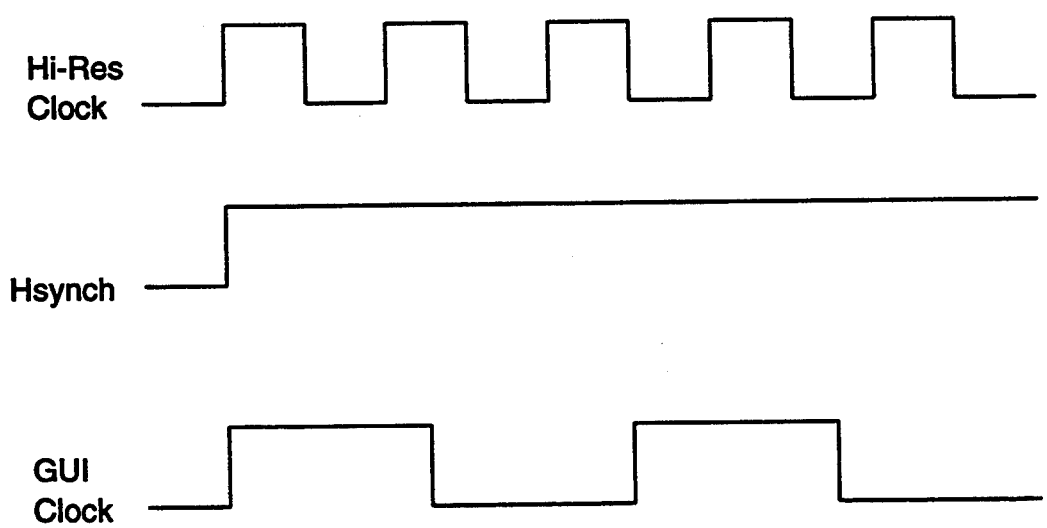
FIG. 3 is a timing diagram associated with the block diagram of FIG. 2.

A timing diagram is shown in FIG. 3 that illustrates the relationship between the clock and Hsync signals. A clock edge from the GUI dot clock is used to trigger the Hsync signal. The Hsync signal is typically a pulse, but is shown as a step function in FIG. 3 due to the disparity in the frequencies between the clock and sync signals. A clock edge of the Hsync signal in turn triggers the high resolution clocks to the video memory 28 and RAMDAC 30.

Figure 4:
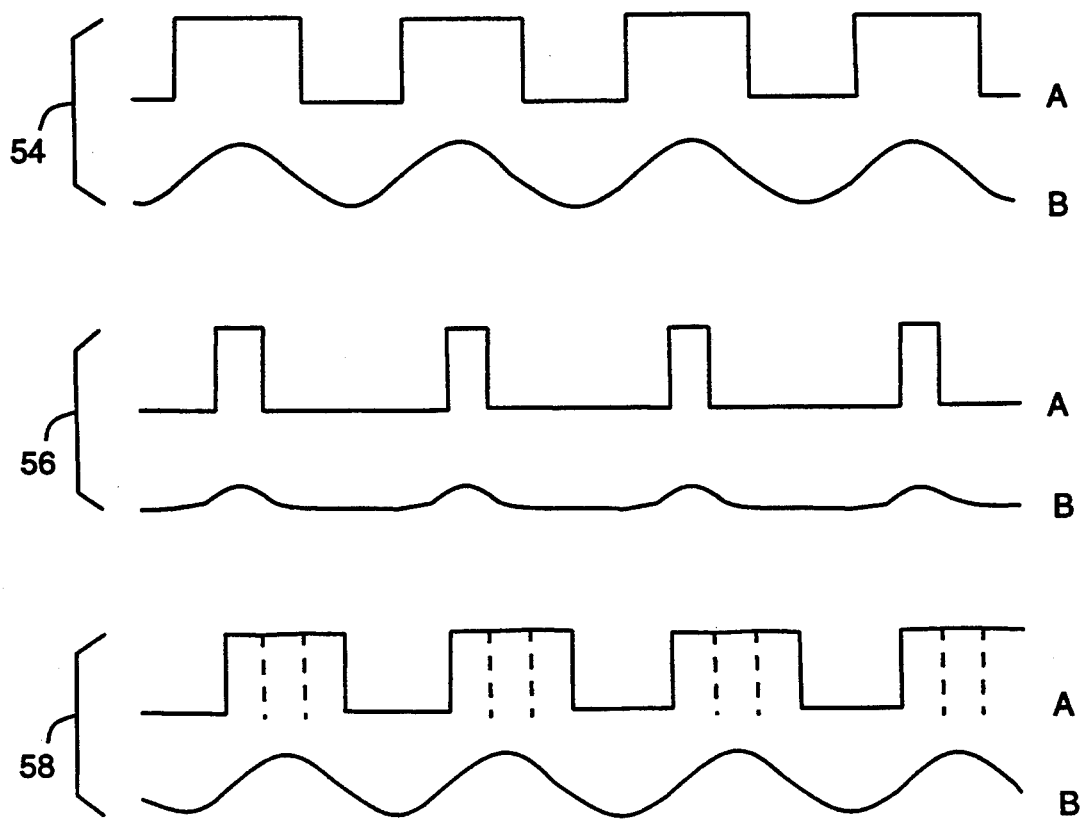
FIG. 4 is a timing diagram illustrating higher and lower resolution video signals according to the present invention.

The improvement in aliasing and resultant high resolution graphics images are illustrated with the waveform pairs 54, 56, and 58 shown in FIG. 4. In each waveform pair, the A waveform is a digital voltage or analog RGB current video data and the B waveform is the intensity of the image as actually displayed on the screen of the video monitor. In waveform pair 54, a low-speed pulse train is shown having a minimum pulse width, corresponding to an individual pixel, that is suitable for being displayed on a raster scan monitor, such as that with a personal computer. The displayed waveform is slightly filtered due to the bandwidth of the video monitor, and the resultant screen intensity represents a fully illuminated pixel alternating with a fully dark pixel. In waveform pair 56, a high-speed video pulse train is shown where each high-speed pulse has a minimum pulse width less than that of the minimum low-speed pulse width, but due to the bandwidth of the video monitor, the resultant screen intensity is not sufficient to fully illuminate each high-speed pixel. In waveform pair 58, a lower frequency pulse train is again shown, but each pulse in the pulse train comprises a packet of three high-speed pulses. The resultant screen image can be easily displayed on the screen, since the minimum pulse width of each packet is at least as great as the minimum low-speed pulse width.

Although, in the specific example of FIG. 4, three high-speed pixel values are used for every packetized pixel, the actual number of high-speed pixels per packet is determined by the ratio of the resolution of the high resolution video stream to the resolution of the low resolution video stream, and, therefore, can on average be a non-integer number. It is important to note that the high-speed packets can be easily phase shifted by one or more high-speed pulse widths to realign the resulting image at the higher resolution. Note that phase shifting by one high-speed pixel is shown between waveform pairs 54 and 58 in FIG. 4. Although the phase shift from scan line to scan line can be made arbitrarily small, the packets can be accurately illuminated if enough high-speed pixels are packed together and the video data stream frequency is approximately equal to the video bandwidth of the monitor.

To display the greater number of pixel values per line stored in the high speed video memory 28 on the same video monitor, the clock rate in the high speed video path must be increased. If the low speed memory 34 has N1 bits of data storage per video line and the high speed memory has N2 bits of data storage, the ratio of N2 to N1 is desirably made equal to the ratio of the high speed clock rate to the low speed clock rate. By changing the clock rates for the respective memories and RAMDACs, the displayed video line will be equal in each graphic plane. In the preferred embodiment, the low speed memory 34 is a video memory having a storage area of about 800 by 600 pixels, and the high speed memory 28 includes two memory sections, each section having a storage area of about 2000 by 600 pixels. The ratio, therefore, of the high speed clock signal frequency to the low speed clock signal frequency is selected to be about 2.5. In the preferred embodiment, the actual low speed clock signal frequency is about 50 MHz divided by four, the number of pixels in the corresponding data output word, and the high speed clock signal frequency is about 125 MHz divided by four, also the number of pixels in the corresponding data output word. The clock frequency at the RAMDACs 36 and 30 is 50 MHz and 125 MHz, respectively.

Figure 5:
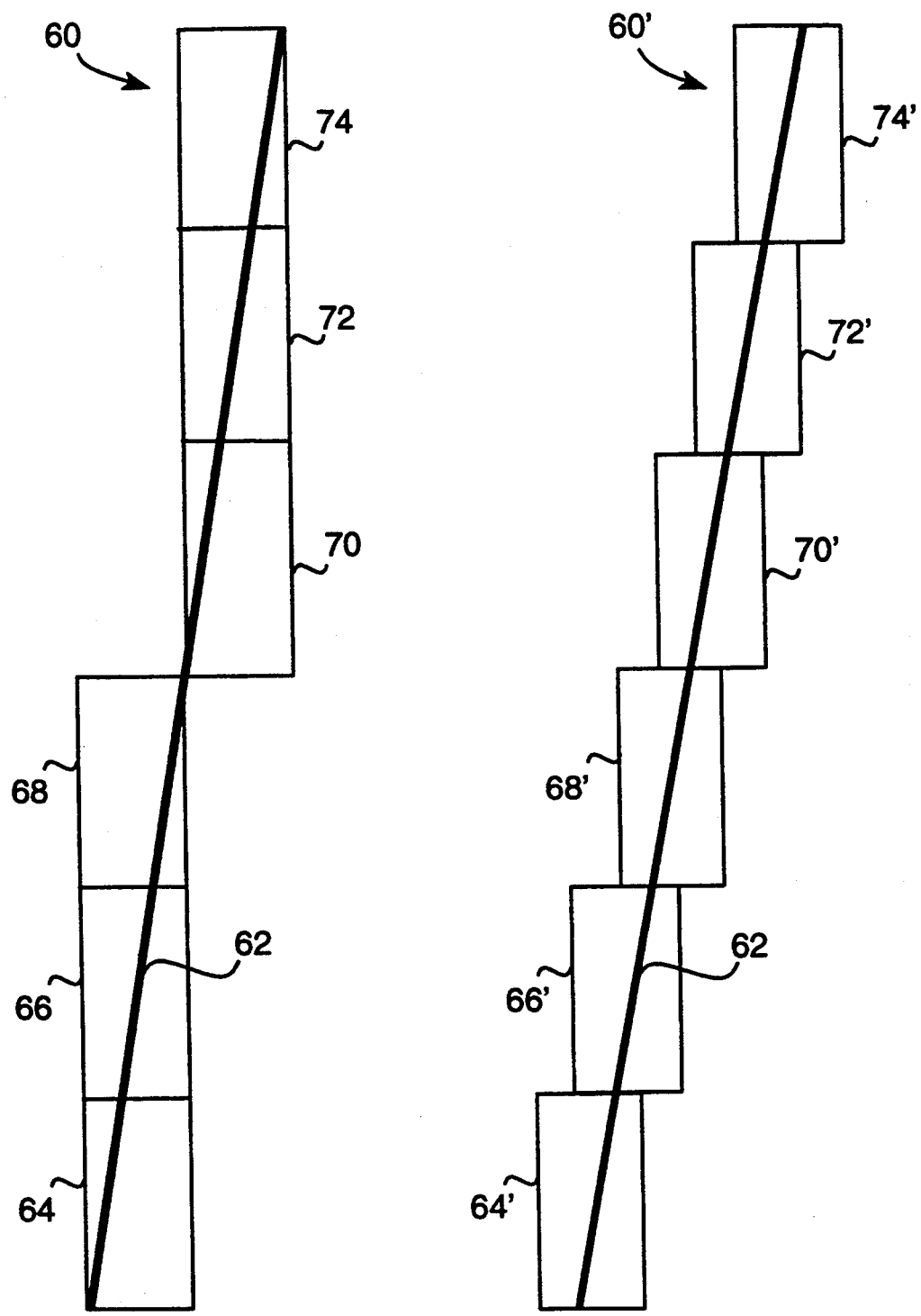
FIG. 5 is a magnified portion of a raster scan display screen showing an aliased line segment and the same segment displayed using the method and apparatus of the present invention.

In FIG. 5, a displayed line segment 60 is shown as approximated by low-resolution pixels on a video monitor. The actual line segment 62 is approximated by six low-resolution pixels 64–74. In the conventional monitor, the pixels can only be shifted by the width of one low-resolution pixel. Therefore, an aliased, jagged edge appears because of the discontinuity between pixels 68 and 70. In the displayed line segment 60' using the method of the present invention, each displayed pixel in the line segment can be shifted by a fraction of a low-resolution pixel. The fraction of the low-resolution pixel is determined by the number of higher frequency pixel values used to construct each pixel. In the example of FIG. 5, three separate higher-resolution pixel values are used to generate each displayed pixel. Therefore, each displayed pixel can be shifted by one-third of a low-resolution pixel width. The resultant displayed line segment 60' therefore has much less aliasing since there is no single abrupt discontinuity between pixels 68' and 70'. Each transition from scan line to scan line is one-third of a low-resolution pixel. The displayed image is much easier to integrate by the human eye and will be deemed to be of a much higher resolution than displayed line segment 60.

Figure 6:
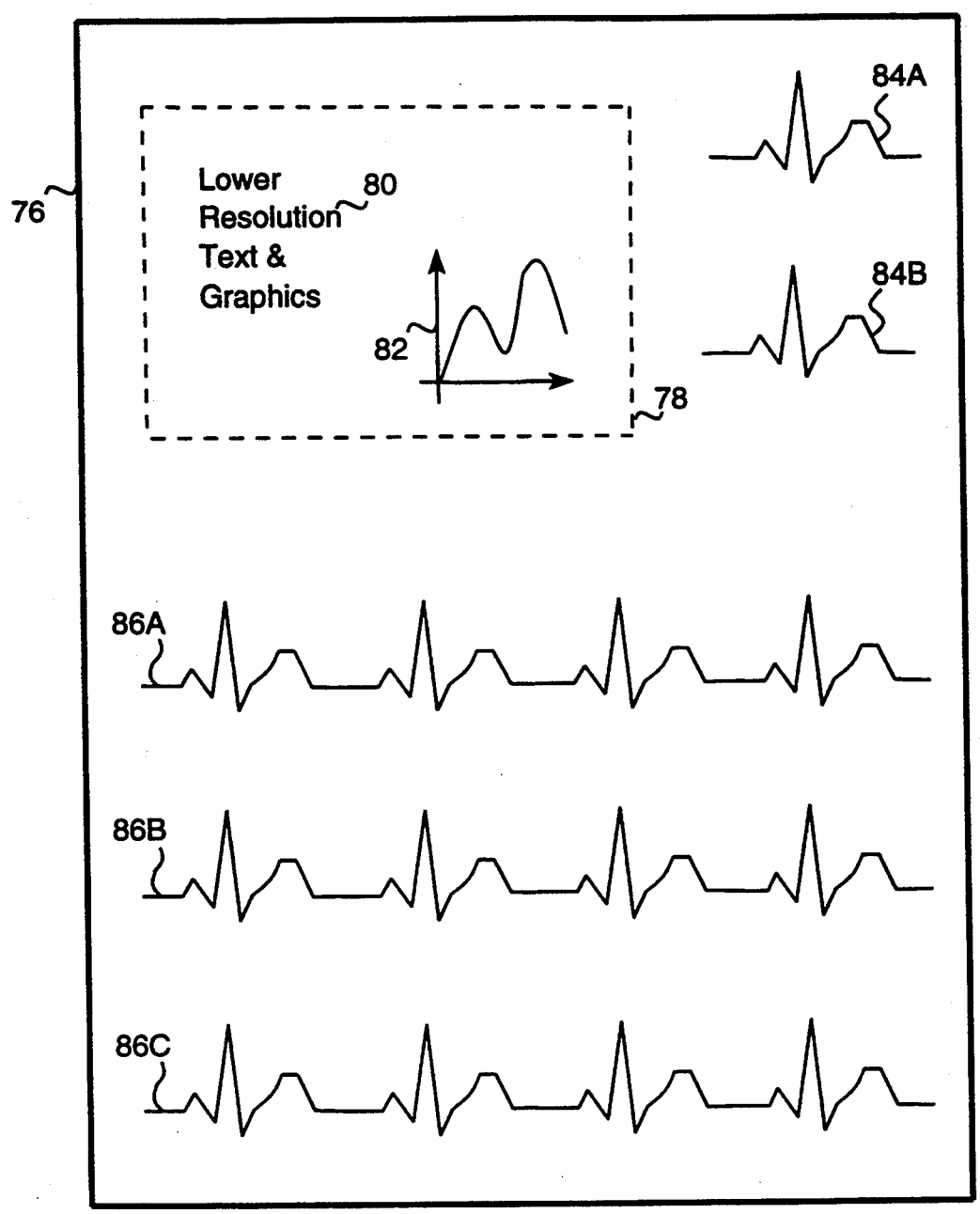
FIG. 6 is a raster scan display screen according to the present invention showing a combined video image containing lower resolution text and graphics, a stationary high resolution ECG waveform field, and a scrolling high resolution ECG waveform field.

FIG. 6 shows a monitor screen 76 displaying a low resolution field 78 as would be found on a personal computer having text 80 and graphics 82 both displayed at a first predetermined resolution. The field 78 can extend throughout the entire screen area 76 or be confined as shown. Simultaneously, one or more channels of scrolling ECG waveforms 86A through 86C are displayed at a second predetermined resolution greater than the first resolution according to the method discussed above. One or more stationary ECG waveforms 84A and 84B are also simultaneously displayed at the second resolution. The high resolution ECG waveforms can be displayed for any arbitrary number of channels and in any position on the screen 76. The stationary ECG waveforms 84A and 84B can be an average or snapshot of one of the displayed scrolling waveforms, or can be an average or snapshot of another non-displayed channel. In the preferred embodiment, memory 28 includes two separate memory locations. A first memory location is used to store data for the scrolling ECG waveform image, and a second memory location is used to store data for the stationary ECG waveform image.

It has been shown that the method for simultaneously displaying images of different resolutions on a video monitor includes the steps of storing data in a first memory having N1 pixel locations per line, generating a first video data at a first rate, storing data in a second memory having N2 pixel locations per line, and generating a second video data stream at a second rate. The ratio of the second rate divided by the first rate is desirably set to be equal to N2 divided by N1. The numbers N2 and N1 are integers, but the ratio need not be an integer. The first and second video data streams are combined and displaying on a commonly available personal computer video monitor. The enhancement in resolution and reduction in aliasing for the high resolution images is possible since successive lines are slightly shifted in increments of single high resolution pixels.

A PREFERRED EMBODIMENT

Figure 7:
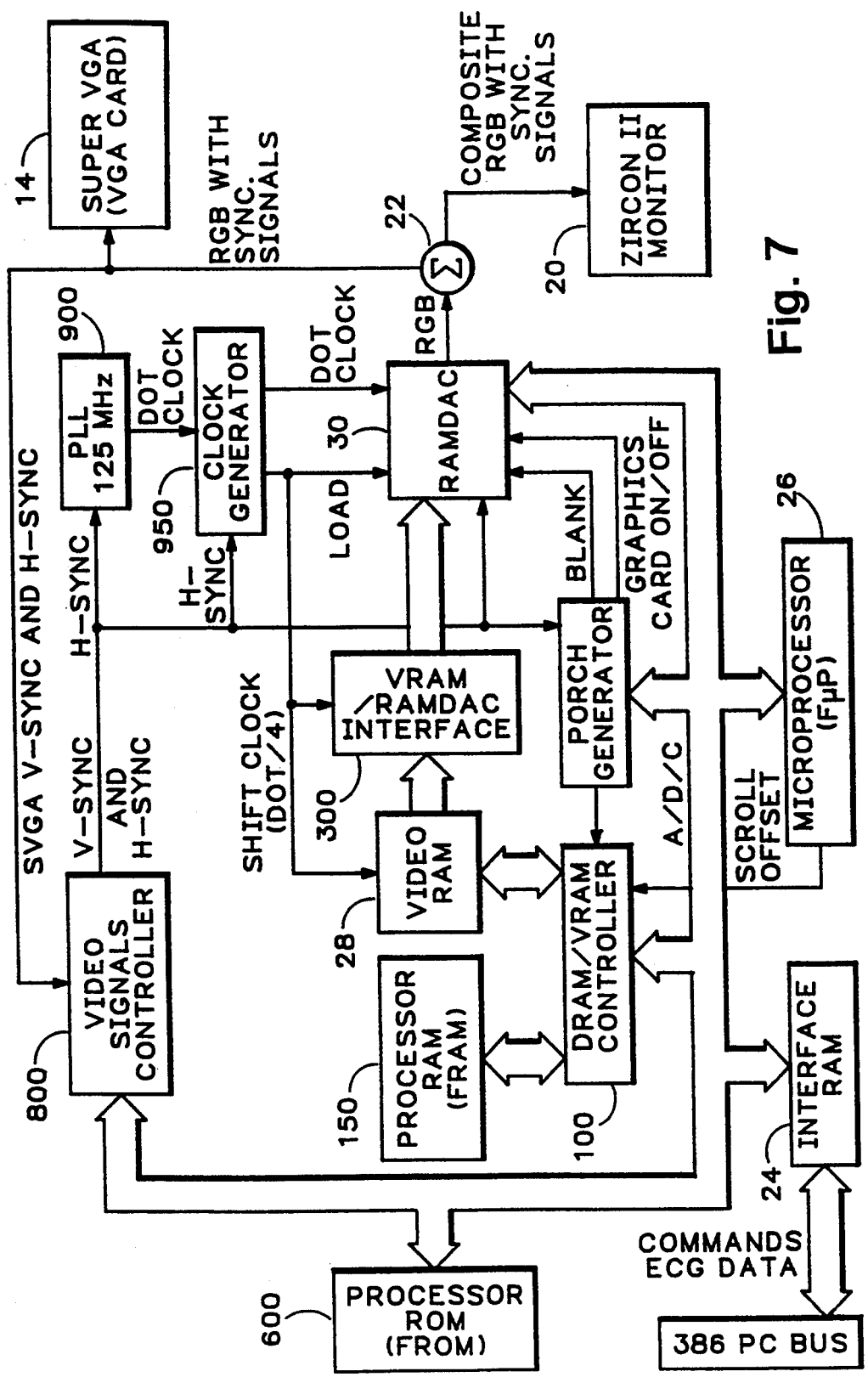
FIG. 7 is a more detailed block diagram of the higher resolution video path.

A more detailed block diagram of the higher resolution video path is shown in FIG. 7. Each of the blocks and related functions in the block diagram is described in further detail below. In the description of the preferred embodiment that follows, the video controller 26 is the 80960CA manufactured by Intel Corp. Other microprocessors or microcontrollers of sufficient computing power, however, can be used.

VRAM/DRAM controller

The VRAM/DRAM controller 100 is a combined DRAM and VRAM controller. The first section of the VRAM/DRAM controller 100, the DRAM controller, controls the interface between the video controller 26 and its corresponding memory 150, preferably DRAM. The second portion, the VRAM controller, controls the interface between the video controller 26 and the VRAM 28. The DRAM controller portion is implemented in a application specific integrated circuit (ASIC) for cost reasons, but can be implemented using a standard DRAM controller compatible with the video controller 26. The separate VRAM controller is desirable because the VRAM has a serial register and a color register not present in DRAM. Additional lines are present to perform transfers from these extra memory segments. Specifically, the VRAM controller portion implements the following basic operations: transferring data between the main memory array of the VRAM and its serial register; writing to the color register; using the color register in write operations; and enabling the use of the write mask functionality of the VRAM. In the preferred embodiment, the VRAM controller is a DP8520 manufactured by National Semiconductor Corporation of Santa Clara, Calif.

The transfers from main memory to the serial register are required for the Video Shift Update (VSUD) operation. The VSUD is a critical portion of the ability to display video memory on a screen. It essentially consists of selecting a given row in the VRAM memory and transferring it to the serial register. The serial register is then the source of the pixel stream to be converted into analog video signals (through the RAMDAC 30 and video mixer 22). Given the critical timing nature of the VSUD, it is desirable to implement the procedure completely in hardware.

Figure 8:
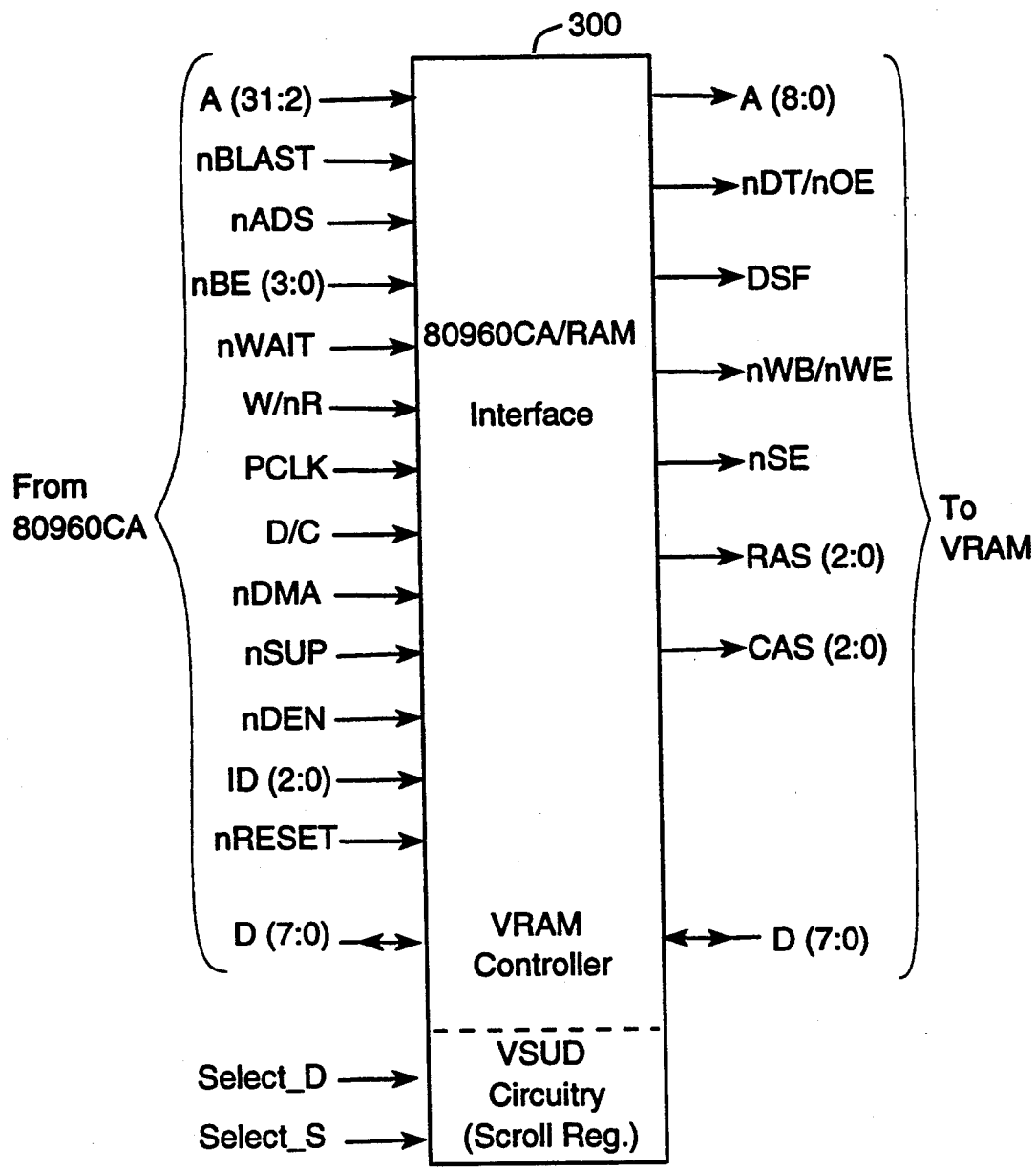
FIG. 8 is an interface showing the input and output signals between the video controller and a typical VRAM.

A display line counter not shown in FIG. 7 is available in the Video Signals controller 800, discussed below, to determine which row of the VRAM is due to be addressed by the VSUD. This counter will track the line number which will be scanned next onto the display. In order to reduce the number of data lines between the VRAM/DRAM Controller 100 and the Video Signals Controller 800, the latter will decode the line number and produce signals Select_D and Select_S. The signals are used to switch the source memory banks for the dynamic and static planes respectively. Infact, these signals are not used by the VRAM/DRAM Controller 100 per se but rather by the VRAM/RAMDAC interface 300. The input and output signals associated with a typical VRAM are shown in FIG. 8.

Additionally, the VSUD hardware generates hardware scrolling (for the dynamic higher resolution plane). Part of the VRAM/DRAM controller 100 consists of a scroll register that contains the starting address of the dynamic plane row. This register is updated by software operating on the video controller 26 such that it will result in the necessary scrolling speed (e.g. 25 mm/s or 50 mm/s). The scroll value is then used when performing the VSUD for the dynamic plane.

In order to make the various write modes available to the VRAM, the same VRAM is mapped several times onto the memory space. The write mode then depends on where the processor writes the information. The VRAM controller is therefore capable of properly decoding the different address regions and executing the corresponding mode. Reading from any of the regions will be the same, consisting of the bit information in the memory (rather than the pixel information).

Dual Port Ram Interface

The interface between the personal computer (PC AT) bus and the video controller 26 is through a 8K×16 bit Dual Port RAM (DPRAM) 24. The current device selection for the DPRAM is an IDT 7025 manufactured by Integrated Device Technology of Sunnyvale, Calif. This part provides semaphore and interrupt logic which is used by the interface protocol.

Figure 9:
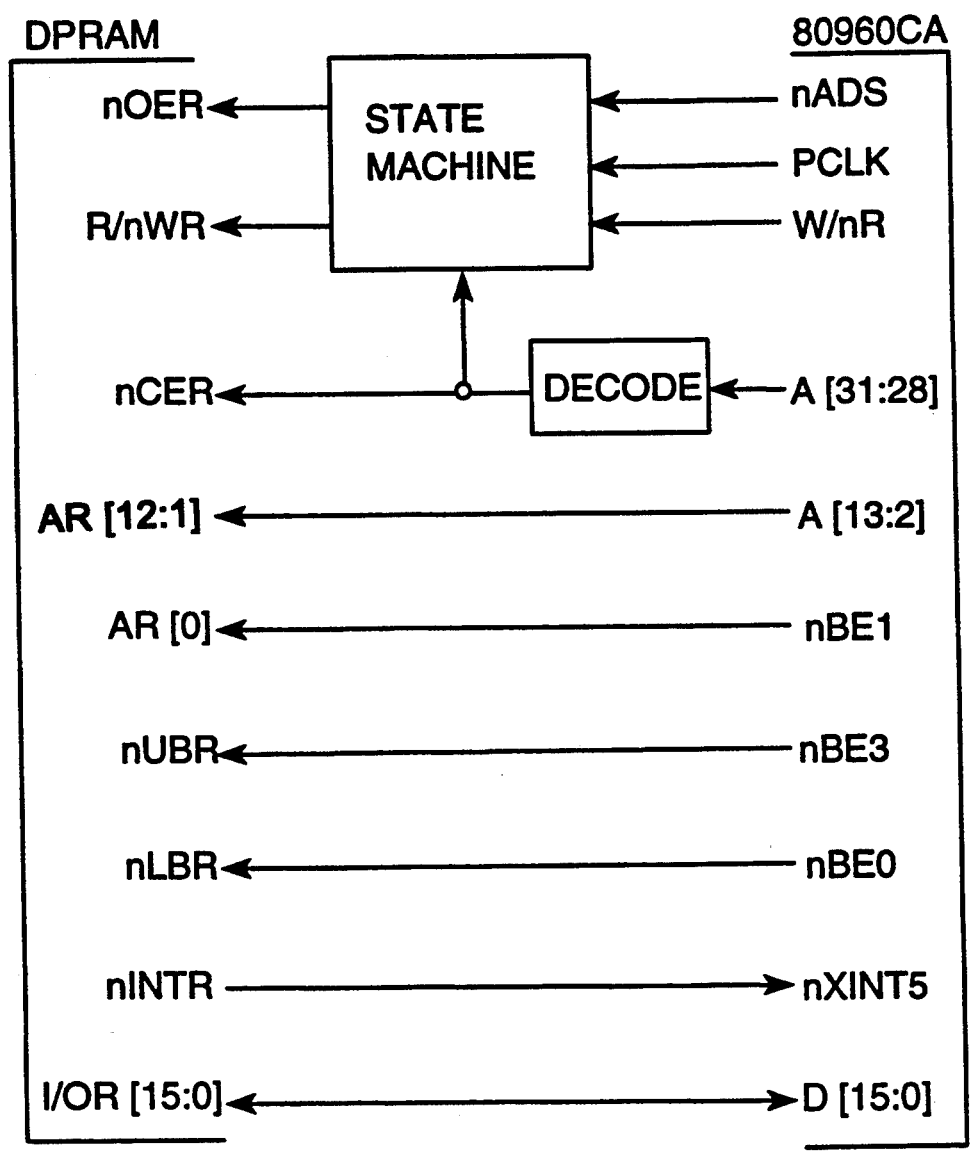
FIG. 9 is a block diagram for the video controller to the Dual Port RAM Interface.

The DPRAM part is mapped into the video controller 26 memory space in segment 9 at address $9000 0000H as a 16 bit device. The 8 semaphore registers are mapped into region 8 at address $8000 0000H. Location $9000 3FFEH in the DPRAM can be written to by the video controller 26 to cause an interrupt on the PC AT bus. Location $9000 3FFCH is used by the PC AT to interrupt the video controller 26 through *XINT5. The interrupt flag in the DPRAM is be cleared in the interrupt service routine by reading or writing to location $9000 3FFCH. The wait state profile for regions 8 and 9 are based on the bus access time of the video controller 26 and the latency of the DPRAM. The circuit diagram for the video controller to Dual Port RAM Interface is shown in FIG. 9.

ROM

The system ROM 600 is used to boot from, do the initial self test, and then load code from the PC into system RAM to be executed. This code is desirably kept to a minimum, fitting easily into a 32K×8 bit ROM. The ROM is mapped into region E of the video controller's 26 memory map at address $EFFF 0000H and region F at address $FFFF 0000H. The Boot ROM is desirably located at $FFFF FF00H for the Initialization Boot Record, IBR.

Video Signals Controller

Figure 14:
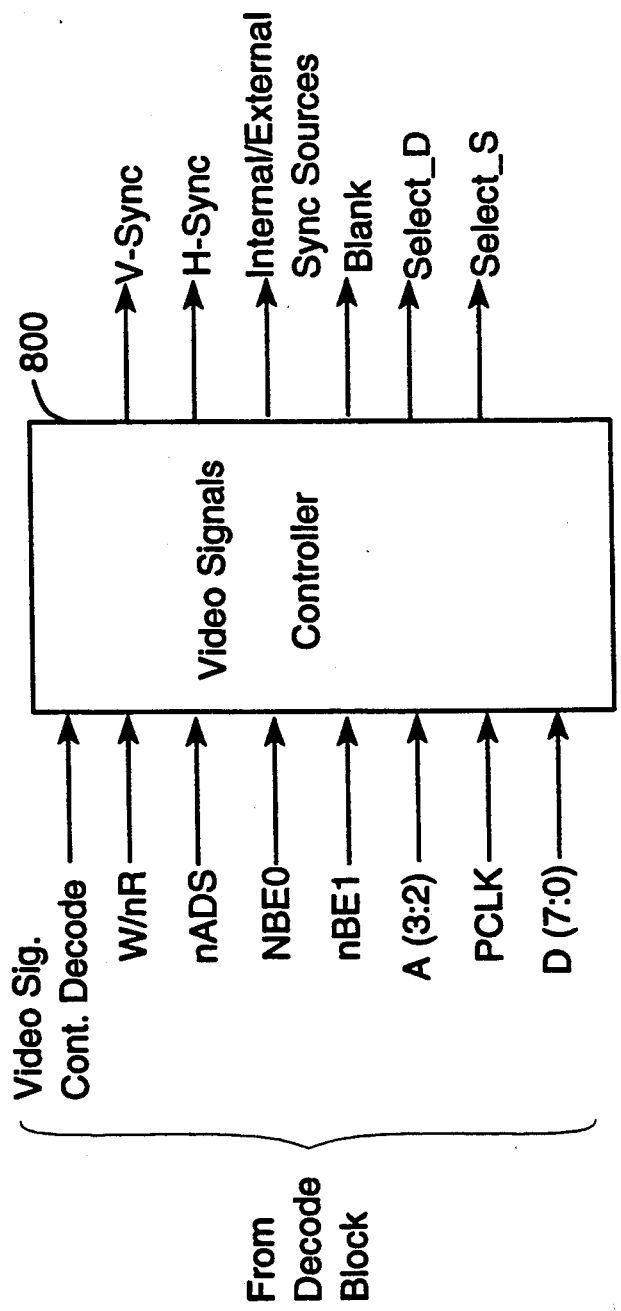
FIG. 14 is a diagram showing the input and output signals for the video controller of FIG. 7.

The Video Signals Controller 800, as shown in FIG. 14, controls several different functions. Its purpose is to setup the video porches (blanked screen areas) and the internal sync source. These two functions are totally programmable by the video controller 26. At power up or reset the Controller starts with default values. Only the required registers can be reprogrammed while the rest retain their default values.

The porches are defined as the blank areas which surround the addressable portion of the screen. The top and bottom regions correspond to the vertical porches and the lateral areas correspond to the horizontal porches. These porches are produced using the BLANK signal of the RAMDAC, which prevents any data received by the RAMDAC from being displayed.

The definition of the four porches logically determines the addressable screen size. In fact, with the current operating mode, not all the of the available VRAM is mapped to the screen. Consider the case of the horizontal porches. The Video RAM buffer within VRAM 28 provides up to 2048 pixels for each line. By defining the size of the two porches, one will also define the actual number of visible pixels on each line. If the porches are large, fewer pixels will be used on each line and there is more blank area to the left and right of the screen. The equivalent is true for the vertical porches.

The porch generator essentially consists of two counters; one that counts the scan lines and one that counts the pixels that have been scanned on the current line. The porches are defined as a given number of lines (vertical) or pixels (horizontal). Thus, the two programmable values are the number of lines corresponding to the top porch and the number of pixels (divided by sixteen) for the left porch.

The hardware activates the BLANK signal while the counters have values less than the programmed values. Once the predefined values are reached the BLANK signal is deactivated. Additionally, the hardware reactivates the BLANK when the limit of resolution plus first porch is encountered.

In the case of the video porches, the programming consists of defining the size of the vertical and horizontal porches. Since all four porches—top, bottom, left, and right—can be programmed, the addressable screen size can vary. Thus, care should be taken to define the porches such that an appropriate visible screen size is produced given the format of the other video signals. Four memory locations are used to define the porch setups.

The internal sync source is used when it is desired to operate the graphics system in a stand-alone mode, either with or without an accompanying low speed video card 14. In this mode there can be no external sync signals for synchronization. Thus, the signals are produced internally. The characteristics of these signals are completely programmable.

The hardware required to implement the internal sync source essentially consists of two counters, one for the horizontal sync and the other for the vertical sync. A full count corresponds to one period of the corresponding signal. When that is reached, the counter resets and continues from the beginning. Each counter works in unison with two registers to produce the appropriate signal.

The two registers define the period of the signal in question and the duration of the SYNC portion of the signal (in effect defining the duty cycle). As the counter passes through the values in the registers the appropriate behavior is produce in the resultant signal. For example, when the counter goes beyond the value in the "SYNC duration" register the sync signal will make the low to high transition. As soon as the period duration is reached the counter is reset and the sync signals makes the negative transition.

The four registers are mapped into the microprocessor memory space so that the sync signals can be fully programmed. The timing of the horizontal sync signal is defined as a given number of periods of the dot clock divided by sixteen. The vertical sync signal is defined as the number of periods of the horizontal sync signal. For example, if a value of four is placed in the SYNC Horizontal Sync Duration Register it means that the SYNC portion of the horizontal sync is four periods of the dot clock divided by sixteen, or 64 periods of the dot clock, e.g., 125 MHz. If such a value were in the corresponding vertical register it would produce a SYNC vertical duration of four horizontal sync periods.

To use the internal sync source, it is required to define the periods, duty cycles, and signal polarity of the horizontal and vertical sync signals. Five memory locations are available for that purpose. Defining that an external sync source is to be used (as in the stand-alone mode) does not permit the user to ignore the other Controller settings. Although external sync signals are used, the Video Signals Controller still has to produce the blank signal. If the internal sync signals and porches are not properly setup the blank signal will not be produced in the required form.

The general video register has three different functions: define the vertical sync period offset, determine the polarity of the sync signals, and select stand-alone operation versus combined operation with an S-VGA card. As with all the other registers, this one also has a default value. This value sets the vertical sync period offset to 512, both sync polarities to active low, and has the graphics system operate in conjunction with an S-VGA card.

The polarity function is necessary given the particular implementation of the Video Signals Controller. Standard operation assumes that both the vertical and horizontal sync signals are active low. However, different applications might require another polarity scheme. Thus, two bits have been set aside to define the polarity of the signals.

The final function determines whether the graphics system will work alone or with an S-VGA card. This basically selects whether the sync signals from the other card are fed through or the Controller's own sync signals are used. Even when the graphics system is setup to work with the S-VGA card, it should be noted that the values in the other registers are still of importance. This is due to the fact that the Video Signals Controller must still produce the blank signal. The register values must work in unison with the external sync signals to produce the correct blank signal. The default values should be sufficient for this purpose.

RAMDAC

Referring back to FIG. 7, the RAMDAC 30 is the portion of the graphics system that is responsible for translating digital pixel data into analog RGB signals. As such, it can be broken down into three major parts: a multiplexer, a color palette, a the triple DAC. The multiplexer takes four or five 8-bit pixels at a time and feeds them one-by-one to access the color palette. The pixel value is used to select a 24-bit color value (8 bits for each primary color), which is then used in the triple 8-bit DACs to produce the corresponding red, green, and blue analog signals. In the preferred embodiment, a Brooktree Bt458 RAMDAC is used.

The programmable color palette of the RAMDAC is the key to the coloring scheme. It consists of 16 entries, each 24 bits wide (8 bits each for the red, green, and blue analog signals), all of which are fully programmable to have any desired color value. The use of a color palette entry is driven by the data in the VRAM. This data is the actual palette entry numbers. Thus, a value of zero in VRAM indicates the use of color zero in the palette, whatever that color value might be. The entry used, however, is determined by the VRAM data for both the static and dynamic planes, as described in the Graphics Plane Mixing section below.

Video Controller/RAMDAC Interface

Figure 10:
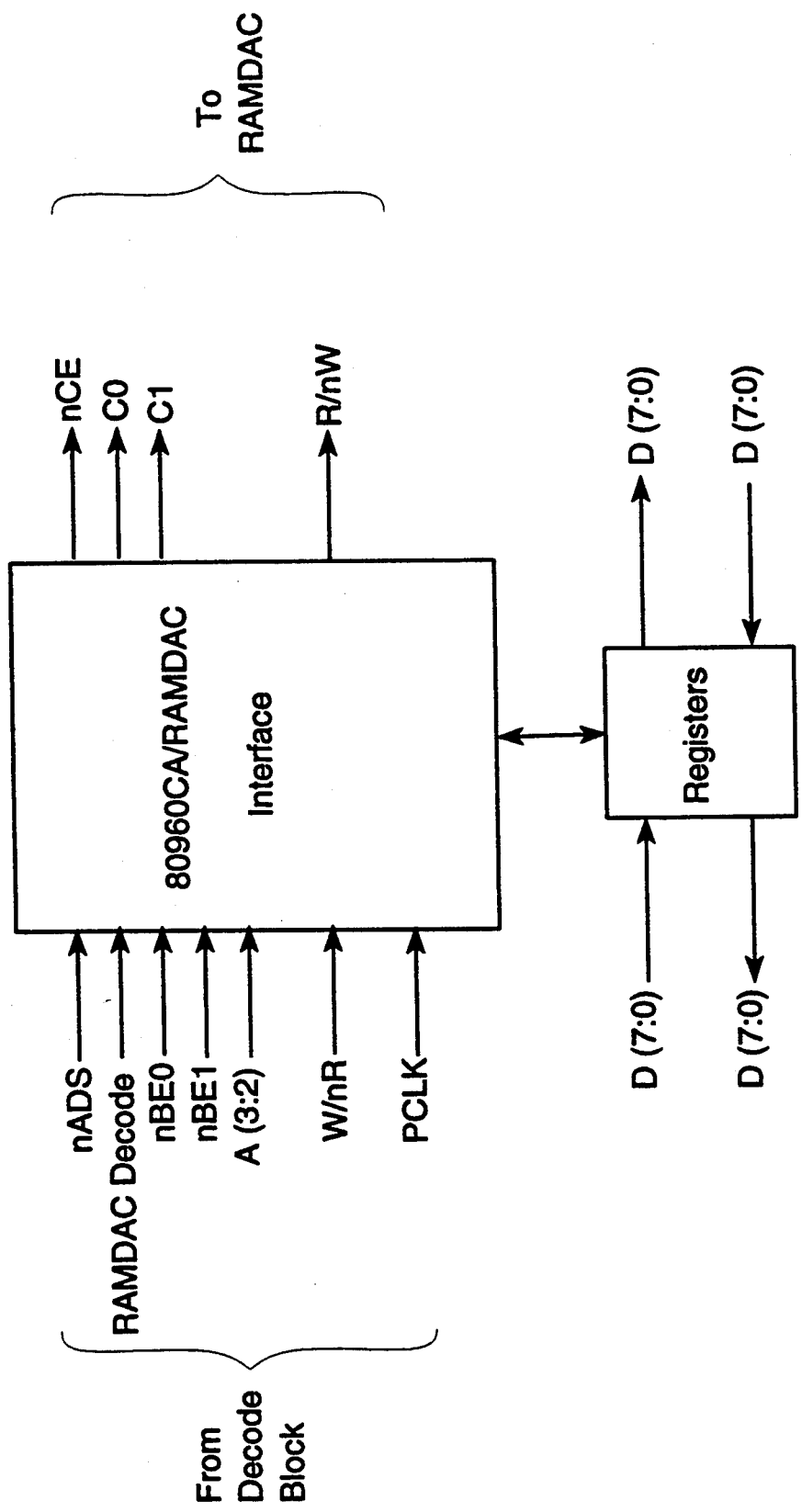
FIG. 10 is an interface between the video controller and the RAMDAC.

Referring now to FIG. 10, the major functions provided by the Video Controller/RAMDAC interface, not shown in FIG. 7, are: to set up the major operating mode (multiplexing scheme, select color palette, blink rates, and overlay enable); set up the read and blink mask registers; initialize the color palette with the necessary color values; and define the overlay colors, if they are being used.

The procedure to write or read data from the RAMDAC is a two step process. The first step is to write the appropriate value to the address register. Then either read or write data to one of the other registers. For example, to specify the value of color 8 in the color palette it is desirable to first write the value 8 to the address register and then write the information to the color palette location.

There are two other registers besides the Address and color Palette registers: the Control and the Overlay color registers. The Control register is actually a conglomeration of four different registers, which are needed to set up the operating mode of the RAMDAC 30.

Graphics Plane Mixing

The mixing mode between the two graphics planes is entirely defined by the colors in the RAMDAC's color palette. Thus, having the dynamic plane write "over" the static plane or the static "over" the dynamic or have the two mix together is done in software.

As can be seen in other sections, the VRAM color data is only two bits deep for each pixel while the RAMDAC pixel port is eight bits in size. What actually happens in the preferred embodiment is that bits 2 and 3 of the RAMDAC port are for the dynamic plane and bits 0 and 1 are for the static plane (bits 4 through 7 are grounded in this implementation). Hence, the combination of the two pixels will access one color in the color palette. This format enables programmable mixing modes.

Consider that in a given location of the screen there is a blue, say dynamic color $01_b$, pixel on the dynamic plane and a red, say static color $10_b$, pixel on the static plane. This combination will access color $00000110_b$, or 6. If a dynamic over static scheme is desired then color 6 of the palette must be defined as blue. For the reverse mode the color should be red, and color 6 could be magenta or some other color if a mixed mode is required.

VRAM/RAMDAC Interface

Figure 11:
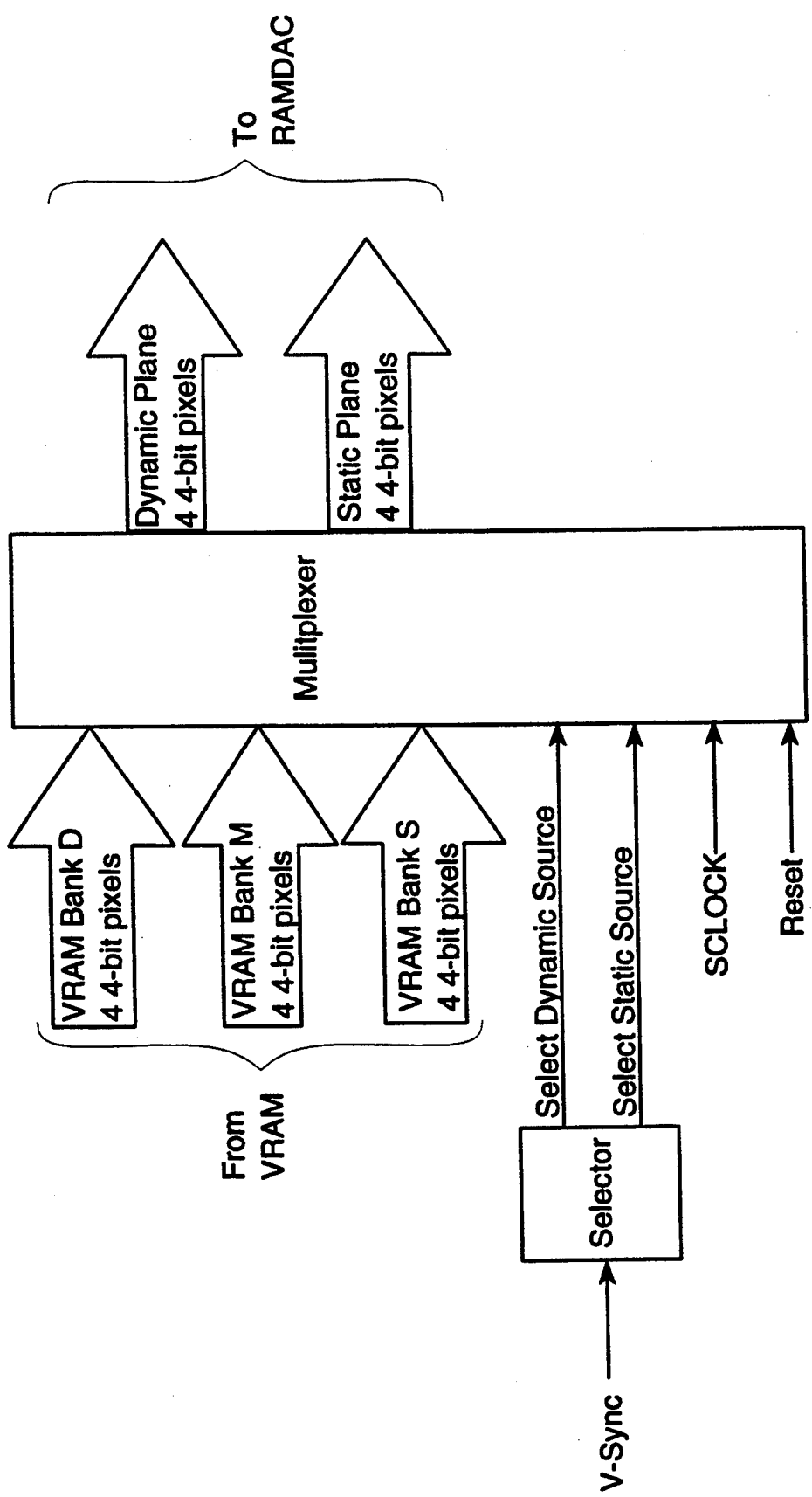
FIG. 11 is an interface between the VRAM and the RAMDAC having a multiplexer for selecting the dynamic and static pixel planes.

Referring now to FIG. 11, the VRAM/RAMDAC interface 300 between the VRAM and the RAMDAC is necessary to be able to implement two graphics planes. In general terms, the VRAM consists of three different banks from which two planes are produced. Each plane receives data from one of two specific banks at any given time. Thus, the main functionality of the interface is to select the appropriate bank for each plane.

Clock Generator Subsystem

Figure 12:
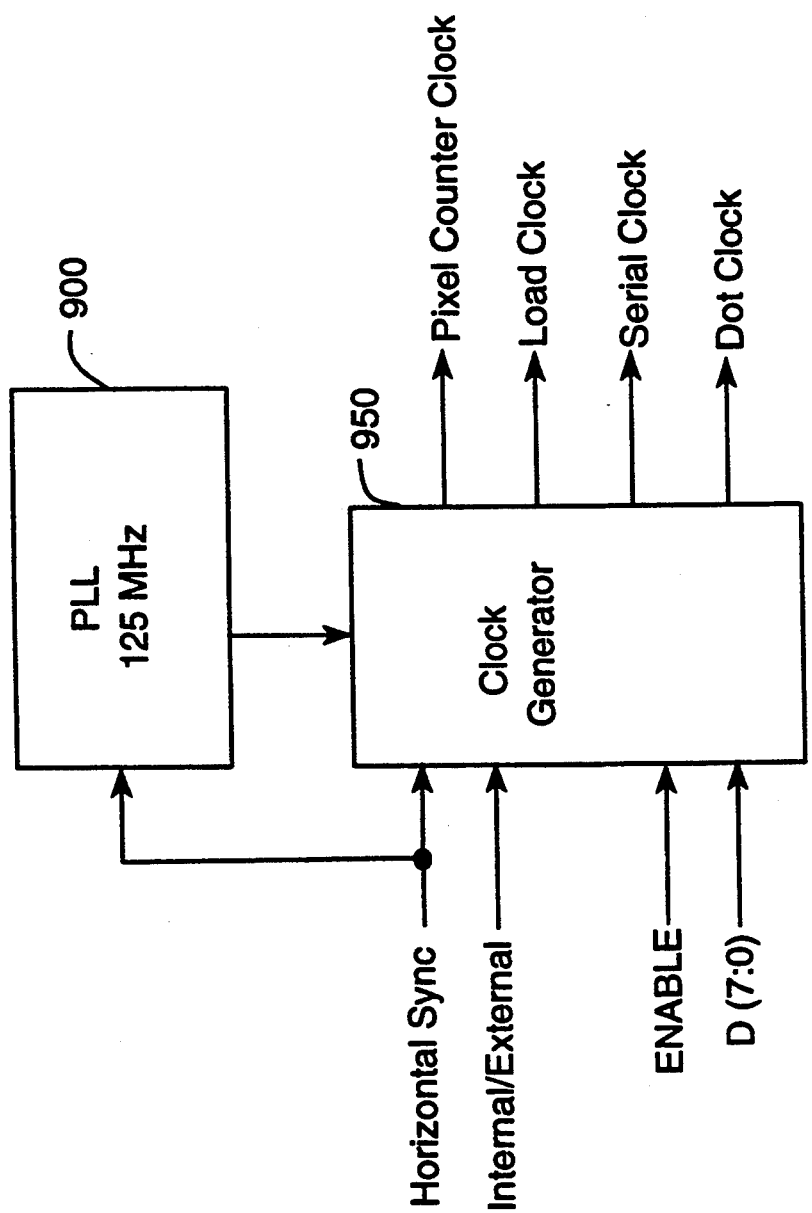
FIG. 12 is a schematic of the clock generator circuit of FIG. 7.

Referring now to FIG. 12, the clock generator subsystem 900 and 950 has the responsibility for several different functions. The foremost function is the synchronization of the dot clock with the external sync signals. Other functions include supplying the signals necessary for clocking out the data from the serial port of the VRAMs, for loading the pixel streams into RAMDAC 30, and to clock the pixel counter portion of the Video Signals Controller 800. The dot clock is 125 MHz.

The dot clock produced by the clock generator 950 must be synchronized with the horizontal sync signal used by the high resolution video section. If this sync signal is produced internally, synchronization is guaranteed by the design. When the sync signal is from an external source, a phase-locked loop (PLL) 900 is used to produce the proper dot clock. In this case, the dot clock can be allowed to jitter up to 3 ns with respect to the horizontal sync.

The VRAM serial clock and the RAMDAC load signal are one fourth of the dot clock frequency, i.e., 31.25 MHz. This value is based upon the fact that four pixels at a time are transferred from the VRAM to the RAMDAC. Both signals are derived from the dot clock to verify synchronization, but the load signal must be delayed from the serial clock. The latter condition is necessary due to the propagation delay inherent in the VRAM/RAMDAC interface.

The signal for the pixel counter of the Video Signals Controller is derived from the dot clock. However, it does not need to be the dot clock itself, thus avoiding the need for more high speed traces and parts. The current solution is to use the VRAM serial clock and just count groups of four pixels. This is entirely acceptable and it is possible that lower frequency signals could be used for the purpose (e.g. groups of ten pixels).

In the preferred embodiment, the clock generator 950 is a National DP8531 Clock Generator manufactured by National Semiconductor of Santa Clara, Calif. The interface consists of an 8-bit register located at location $5090 0000H in the video controller memory map. This interface register is the gateway to the sixteen internal registers of the clock generator. The top four bits of the interface register specifies one of the sixteen clock generator registers while the bottom four bits contains the data to be written to the internal register.

Video RAM Subsystem

Figure 13:
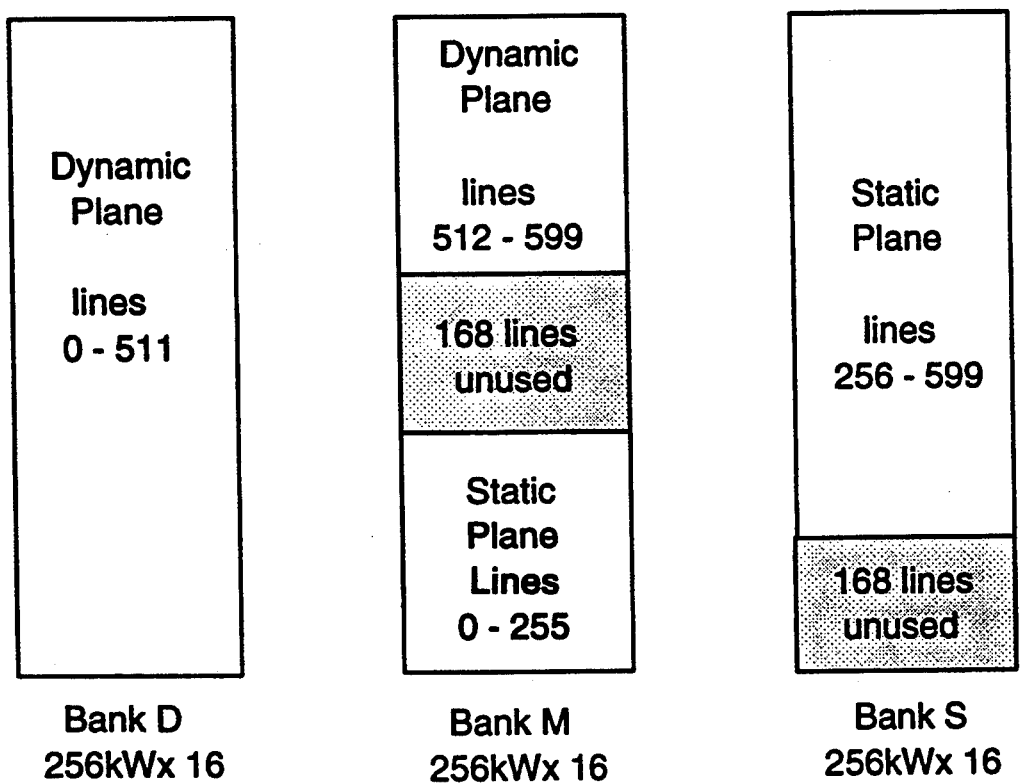
FIG. 13 is a diagram showing the VRAM allocation to the various graphics planes.

Referring now to FIG. 13, the VRAM 28 is comprised of three banks, each consisting of two 1Mbit chips. Each VRAM is a 512×512 block which is four bits deep. Thus, each bank is a 512×512 by 8 segment.

In order to implement a 2000×600 screen, each graphics plane encompasses two banks. One bank is split up equally between the two planes, so in actuality each plane has 768 lines available, which can be used to support other plane organizations such as 1700×768. Each pixel consists of two bits that form the color information. Thus, given the 8 bit-wide nature of the VRAM up to 4 continuous pixels can be written in a normal write cycle. In a block write cycle up to 16 pixels can be written.

Video Mixer Subsystem

The video mixer 22, previously referred to as the summer 22 in FIGS. 1, 2, and 7, takes the S-VGA RGB signals and the high resolution RGB signals, and mixes or combines them together to produce one set of RGB signals for the monitor. Mixing can take on a variety of forms (e.g. adding, "maxing", muxing, etc.), but the adding mode has been selected. However, it is apparent to those skilled in the art that the two RGB signals can be combined by multiplexing between the two signals depending on whether the S-VGA RGB signal or the high resolution RGB signal should be displayed. Therefore, if the S-VGA background is exactly the same color as the high resolution ECG traces, the latter is still visible to some extent.

The video mixer 22 has a proper bandwidth corresponding to the bandwidth of the analog RGB signals, as well as impedance matching on all three ends (S-VGA, high resolution, and monitor). Given that the high resolution dot clock is 125 MHz, the bandwidth should be at least twice that to maintain some sharpness in that signal's edges. However, more bandwidth than that is probably not necessary because it would surpass the bandwidth of the video amplifiers of the monitor itself.

Impedance matching should be such that the circuit represents 75 Ohms at all of its inputs and outputs. This reduces reflections and improves performance. Ideally, the video mixer 22 should have no inherent gain or loss. However, since brightness and contrast can be adjusted on the monitor, some loss or gain is acceptable.

Screen Data Organization

Figure 15:
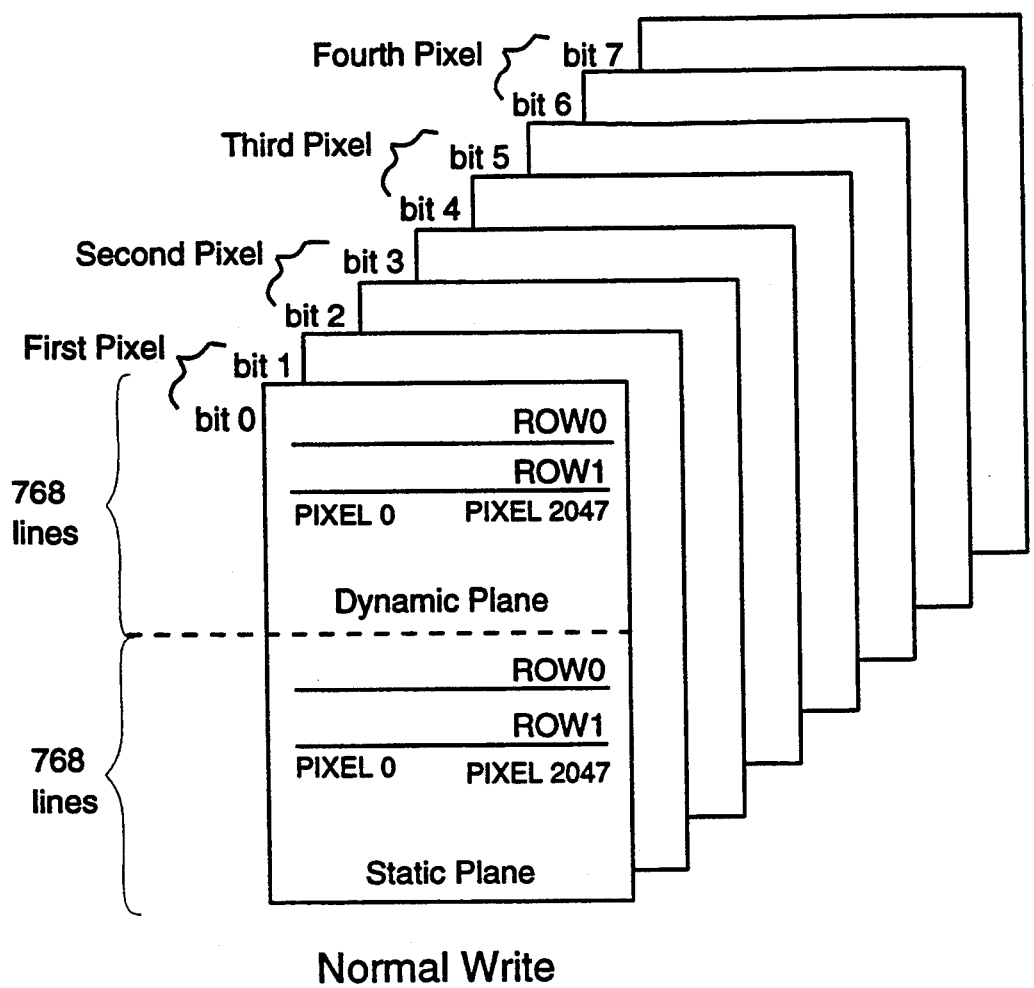
FIG. 15 is a diagram showing the VRAM organization for a normal write operation.

The VRAM is organized as an 8-bit memory in two different regions. The two regions cover the same VRAM but implement two different write methods. The first write method is depicted in FIG. 15. This is called the normal write region because one has to write every bit of each pixel. Since each pixel is two bits, the two LSBs correspond to the first pixel in the 8-bit data, the next two bits correspond to the second pixel, and so on. On the screen, the second pixel is to the right of the first pixel, the third to the right of the second, and the fourth pixel to the right of the third. Thus, one write to the normal write region will define four consecutive pixels.

Figure 16:
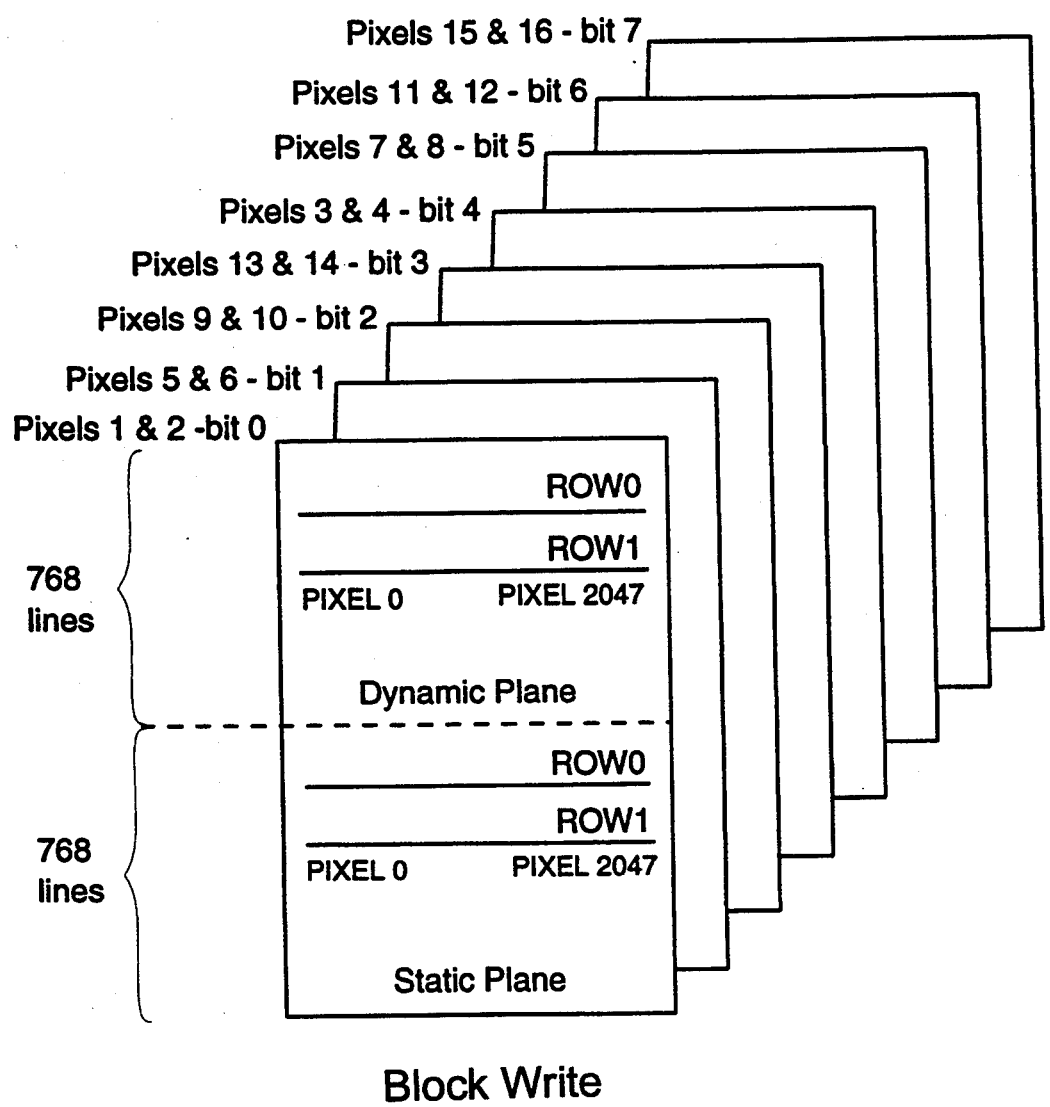
FIG. 16 is a diagram showing the VRAM organization for a block write operation.

FIG. 16 depicts the block write VRAM region block write is one that uses the color register to write data to VRAM 28. The data being sent to VRAM 28 is used as a mask to determine whether or not to write the color register. This region is best used to do block fills of a particular pattern or color. One VRAM write can determine as many as 16 pixels. The data is shown on the screen from left to right from pixel 1 to pixel 16.

The color register has an awkward mapping to the pixels written in a block-region write. The simplest method of exposure is to present a table and let the reader compare it with FIG. 16 to produce some kind of correspondence.

| Color Register Bits | Pixels Affected |
|---|---|
| 0, 1 | 1, 5, 9, 13 |
| 2, 3 | 2, 6, 10, 14 |
| 4, 5 | 3, 7, 11, 15 |
| 6, 7 | 4, 8, 12, 16 |

To further clarify, consider that a specific block-region write has bit 7 high. This indicates that pixels 15 and 16 are written with the color register value. Thus, pixel 15 has the color corresponding to the register's bits 4 and 5 and pixel 16 will have the color determined by bits 6 and 7. Note that since this type of write covers 16 pixels worth of data and each address location corresponds to 4 pixels there is more than one way to write to a given pixel. A given pixel is pixel 1 in address "x", pixel 4 in address "x-1", pixel 8 in address "x-2", pixel 12 in address "x-3", and pixel 16 in address "x-4".

The scroll register is used to implement scrolling on the dynamic plane. A row/line of the dynamic plane can be displayed at any arbitrary location. The scroll register supplies that information to VRAM Controller 100. Therefore, changing the value in the scroll register changes the position of VRAM data on the screen, and, used appropriately, can produce a certain scrolling speed.

The value in the register points to a specific address in a VRAM row. Since each location contains four pixels (see FIG. 15), scrolling at the VRAM level can only be accomplished in steps of four pixels. Since a row contains 2048 pixels, the scroll register value range is between 0 and 511. Values beyond 511 will "wrap around" (e.g. 512 will actually be seen as 0). Since the scroll register is in 8-bit memory, there are two contiguous memory locations required. In order to implement scrolling finer than 4-pixel steps, two more bits are used in the scroll register. These bits are used in VRAM/RAMDAC interface 300 to offset into the 4-pixel packet. For example, if initially all four pixels went straight through the interface to the RAMDAC 30 and the scroll register bits were set to scroll by one, VRAM/RAMDAC interface 300 would only get the second, third, and fourth pixels of the current packet, append the first pixel of the next packet behind the fourth pixel, and send the newly created packet to RAMDAC 30.

Implementing the scrolling function proceeds by using the Vertical Sync signal as a timer. At the beginning of each V-sync, the scroll register is incremented by an appropriate value. For example, given a data set of 200 samples/inch and 25 mm/s scroll speed, the scroll register is updated approximately 200 pixels/s (assuming 1 sample per pixel). To best approximate 200 pixels/s, if the V-Sync frequency is 72 Hz, the scroll register is incremented by 3 (pixels) each V-sync.

Having described and illustrated the principles of the invention in a preferred embodiment thereof, it is apparent to those skilled in the art that the invention can be modified in arrangement and detail without departing from such principles. I therefore claim all modifications and variation coming within the spirit and scope of the following claims.

I claim:

1. A method for simultaneously displaying images of different resolutions on a video monitor having a finite bandwidth defining a minimum pulsewidth for illuminating a pixel, the method comprising the steps of:

storing data in a first memory, the data in the first memory representing a first video frame having N1 pixels per line;

generating a first video data stream from the first memory at a first rate having a first display pixel pulsewidth at least as great as said minimum pulsewidth;

storing data in a second memory, the data in the second memory representing a second video frame having N2 pixels per line, wherein N1 and N2 are positive integers and N2>N1;

generating a second video data stream from the second memory at a second rate in excess of the video monitor bandwidth, wherein the ratio of the second rate divided by the first rate is approximately equal to N2 divided by N1;

packetizing the second video data stream into display pixels each having a second display pixel pulsewidth at least as great as said minimum pulsewidth to produce a second displayable video data stream:

combining the first video data stream and the second displayable video data stream to produce a combined video data stream; and displaying the combined video data on the video monitor.

2. A method as in claim 1 in which the step of storing data in the second memory comprises the step of storing at least two pixel values to represent a displayed pixel on the video monitor.

3. A method as in claim 1 in which the step of storing data in a first memory comprises the step of storing data representing text and graphics at a first predetermined resolution.

4. A method as in claim 3 in which the step of storing data in a second memory comprises the step of storing data representing a biological waveform at a second predetermined resolution greater than the first resolution.

5. A method as in claim 1 in which the step of displaying the combined video data on a low resolution video monitor comprises the steps of:

displaying a text and graphics field at a first predetermined resolution; and simultaneously displaying a ECG waveform image at a second predetermined resolution greater than the first resolution.

6. A method as in claim 1 in which the step of displaying the combined video data on a low resolution video monitor comprises the steps of:

displaying a text and graphics field at a first predetermined resolution;

simultaneously displaying a scrolling ECG waveform image at a second predetermined resolution greater than the first resolution; and simultaneously displaying a stationary ECG waveform image at the second resolution.

7. A method as in claim 1 further comprising:

horizontally and vertically synchronizing the first video data stream and the second displayable video data stream: and offsetting a first display pixel in a first scan line from a second display pixel in a second scan line adjacent the first scan line by an amount less than said minimum pulsewidth.

8. A video graphics system for displaying waveforms on a video monitor having a finite bandwidth defining a minimum pulsewidth for illuminating a pixel comprising:

a first memory for storing a first video image having a first horizontal resolution;

means for clocking data out of the first memory at a first rate to provide a first video data stream having a first display pixel pulsewidth at least as great as said minimum pulsewidth;

a first RAMDAC having a digital input for receiving the first video data stream, and an analog RGB current output;

a second memory for storing a second video image having a second horizontal resolution;

means for clocking data out of the second memory at a second rate in excess of the video monitor bandwidth to provide a second video data stream;

means for packetizing the second video data stream into display pixels each having a second display pixel pulsewidth at least as great as said minimum pulsewidth to produce a second displayable video data stream:

a second RAMDAC having a digital input for receiving the second displayable video data stream, and an analog RGB current output;

means for synchronizing the first video data stream and second displayable video data stream; and means for combining the analog RGB current outputs from the first and second RAMDACs to form a combined analog RGB current output.

9. A video graphics system as in claim 8 wherein the video monitor has an RGB input for receiving the combined analog RGB current output.

10. A video graphics system as in claim 8 in which ratio of the second rate to the first rate is equal to the second horizontal resolution divided by the first horizontal resolution.

11. A video graphics system as in claim 8 in which data stored in the first memory represents text and graphics data of a first predetermined resolution suitable for display on a home computer display terminal.

12. A video graphics system as in claim 8 in which the second memory comprises two separate memory locations, a first memory location storing data for a scrolling image of a second predetermined resolution greater than the first resolution, and a second memory location storing data for a stationary image of the second resolution.

13. A video graphics system as in claim 8 in which the means for synchronizing the first and second video streams comprises a phase-locked loop having an input for receiving a horizontal sync signal and an output for providing a high-resolution dot clock to the second memory.

14. A video graphics system comprising:
a video monitor having a finite bandwidth defining a minimum pulsewidth for illuminating a pixel, horizontal and vertical sync inputs, and an RGB input;
a first memory for storing a first video image represented by a first number of low-resolution pixels per horizontal line, the first memory having a clock input and a data output;
a first RAMDAC having a digital input coupled to the data output of the first memory, a clock input, and an analog RGB current output;
a sync generator having a clock input, a horizontal sync output coupled to the monitor horizontal sync input, and a vertical sync output coupled to the monitor vertical sync input;
a system clock generator for providing a low speed clock to the clock input of the first memory, first RAMDAC, and sync generator;
a second memory for storing a second video image represented by a second number of high-resolution pixels per horizontal line, the second memory having a clock input and a data output and the high resolution pixels having a pulsewidth less than said minimum pulsewidth;
means for packetizing the high resolution pixels into display pixels each having a second display pixel pulsewidth at least as great as said minimum pulsewidth;
a second RAMDAC having a digital input coupled to the data output of the second memory, a clock input, and an analog RGB current output;
a phase-locked loop having an input coupled to the horizontal sync output of the sync generator, and an output for providing a high speed clock having a frequency in excess of the video monitor bandwidth to the clock input of the second memory and second RAMDAC; and
a summer having first and second inputs for receiving the analog RGB current outputs from the first and second RAMDACs, and an output coupled to the monitor RGB input for providing a composite RGB current output.

15. A video graphics system as in claim 14 in which the ratio of the high speed clock signal frequency to the low speed clock signal frequency is equal to the second number of high-resolution pixels per line divided by the first number of low-resolution pixels per line.

16. A video graphics system as in claim 14 in which the first memory comprises a memory having a capacity of about 800 by 600 low-resolution pixels, the second memory comprises a memory having a capacity of about 2000 by 600 high-resolution pixels, and the ratio of the high speed clock signal frequency to the low speed clock signal frequency is about 2.5.

17. A video graphics system as in claim 14 in which the first memory comprises a memory having a capacity of about 1024 by 768 low-resolution pixels, the second memory comprises a memory having a capacity of about 1700 by 768 high-resolution pixels, and the ratio of the high speed clock signal frequency to the low speed clock signal frequency is about 1.66.

18. A video graphics system as in claim 14 in which the low speed clock signal frequency at the first memory is about 50 MHz divided by the number of low-resolution pixels in a corresponding data output word, and the high speed clock signal frequency at the second memory is about 125 MHz divided by the number of high-resolution pixels in a corresponding data output word.

19. A video graphics system as in claim 14 in which the low resolution video monitor has a video bandwidth of about 50 MHz.

20. A method for improving the resolution of a video display comprising the steps of:
receiving a first video pulse train comprised of a series of low-speed pulses, each low-speed pulse having a minimum low-speed pulse width corresponding to an individual low-resolution pixel on the display;
receiving a second video pulse train comprised of a series of high-speed pulses, each high-speed pulse having a minimum high-speed pulse width less than the minimum low-speed pulse width corresponding to a high-resolution pixel;

packetizing the high-speed pulses into high-speed packets wherein each packet has a minimum pulse width at least as great as the minimum low-speed pulse width;

combining the first video pulse train and the high-speed packets to form a combined video pulse train; and displaying the combined video pulse train on the video display.

21. A method for improving the resolution of a video display, the display equipped to receive a series of low-speed pulses, each pulse having a minimum low-speed pulse width corresponding to an individual pixel on the display, the method comprising the steps of:

receiving a high-speed pulse train comprised of a series of high-speed pulses, each high-speed pulse having a minimum high-speed pulse width less than the minimum low-speed pulse width corresponding to a high-resolution pixel;

packetizing the high-speed pulses into high-speed packets wherein each packet has a minimum pulse width at least as great as the minimum low-speed pulse width; and displaying the high-speed packets on the video display.

22. A method for improving the resolution of a video display according to claim 21 further comprising the step of selectively phase shifting the high-speed packets by one or more high-speed pulse widths.

* * * * *